(12) United States Patent
Richards

(10) Patent No.: US 11,187,422 B1
(45) Date of Patent: Nov. 30, 2021

(54) AIR PURIFIER/CONDITIONER (APC)

(71) Applicant: Clyde Richards, Los Lunas, NM (US)

(72) Inventor: Clyde Richards, Los Lunas, NM (US)

(*) Notice: Subject to any disclaimer, the term of this patent is extended or adjusted under 35 U.S.C. 154(b) by 0 days.

(21) Appl. No.: 17/060,257

(22) Filed: Oct. 1, 2020

(51) Int. Cl.
| | |
|---|---|
| *F24F 8/10* | (2021.01) |
| *B01D 35/06* | (2006.01) |
| *B01D 47/06* | (2006.01) |
| *F24F 3/14* | (2006.01) |
| *F24F 8/192* | (2021.01) |
| *F24F 8/22* | (2021.01) |
| *F24F 8/117* | (2021.01) |

(52) U.S. Cl.
CPC ............... *F24F 8/10* (2021.01); *B01D 35/06* (2013.01); *B01D 47/06* (2013.01); *F24F 3/14* (2013.01); *F24F 8/192* (2021.01); *F24F 8/117* (2021.01); *F24F 8/22* (2021.01); *F24F 2003/144* (2013.01)

(58) Field of Classification Search
CPC ........ B01D 47/00; B01D 47/06; B01D 35/06; F24F 8/10
See application file for complete search history.

(56) References Cited

U.S. PATENT DOCUMENTS

| | | | | |
|---|---|---|---|---|
| 3,681,896 | A * | 8/1972 | Velkoff | ........... F28F 13/16 96/27 |
| 6,156,098 | A | 12/2000 | Richards | |
| 2009/0263293 | A1* | 10/2009 | Motegi | ........... B03C 3/16 422/122 |

* cited by examiner

*Primary Examiner* — Robert A Hopkins
(74) *Attorney, Agent, or Firm* — William & Myers, P.C.; Jeffrey D. Myers

(57) ABSTRACT

An air purifier and conditioner (and concomitant method of simultaneously purifying and conditioning air) comprising a housing receiving source air and an aqueous solution, a drop charger receiving the source air and providing a spray of electrically charged drops of the aqueous solution to produce treated air, a mist eliminator eliminating liquid in the treated air and producing conditioned air, a heat exchanger receiving the conditioned air and producing supply air, and a fan moving the supply air to a facility employing the supply air.

18 Claims, 11 Drawing Sheets

Aerosol Particle Size:
- • 0.12 microns diameter
- ○ 1.0 microns diameter
- ∗ 5.0 microns diameter
- + 10.0 microns diameter Liquid-To-Gas Ratio: 20 gpm/1,000 cfm Normalized Concentration Residence Time, seconds

*FIG. 3*

AIR PURIFIER/CONDITIONER (APC)

CROSS-REFERENCE TO RELATED APPLICATIONS

Not Applicable.

STATEMENT REGARDING FEDERALLY SPONSORED RESEARCH OR DEVELOPMENT

Not Applicable.

NAMES OF PARTIES TO JOINT RESEARCH AGREEMENT

Not Applicable.

REFERENCE TO A SEQUENCE LISTING, A TABLE, OR A COMPUTER PROGRAM LISTING COMPACT DISC APPENDIX

Not Applicable.

STATEMENT REGARDING PRIOR DISCLOSURES BY THE INVENTOR OR A JOINT INVENTOR

Not Applicable.

BACKGROUND OF THE INVENTION

Field of the Invention (Technical Field)

The present invention relates to an apparatus and method to remove and destroy pathogens and toxic gases from air and simultaneously condition an air supply, especially for buildings.

DESCRIPTION OF RELATED ART

The present invention (Air Purifier/Conditioner, or APC) improves upon conventional HVAC (Heating, Ventilation and Air Conditioning) systems in a number of ways. In conventional systems, if any aerosol removal is performed, it is performed by filters made of small fibers. The APC does not require fiber filters.

Conventional HVAC systems do not expose the source air directly to liquid except during humidification. The APC exposes the source air to copious amounts of an aqueous solution in the form of electrically charged water drops.

Conventional HVAC systems do not use electrically charged liquid drops. The APC uses the drop charging method as taught by Richards (U.S. Pat. No. 6,156,098) and in use today in many industrial gas cleaning applications.

BRIEF SUMMARY OF THE INVENTION

The present invention is of an air purifier and conditioner comprising: a housing receiving source air and an aqueous solution; a drop charger receiving the source air and providing a spray of electrically charged drops of the aqueous solution to produce treated air; a mist eliminator eliminating liquid in the treated air and producing conditioned air; a heat exchanger receiving the conditioned air and producing supply air; and a fan moving the supply air to a facility employing the supply air. The invention can additionally comprise a liquid purifier providing the aqueous solution, preferably wherein the liquid purifier maintains a concentration of one or more disinfectants to destroy pathogens and other infectious agents and/or wherein the liquid purifier exposes the aqueous solution to ultraviolet light to destroy pathogens and other infectious agents. The invention provides at least 99.6% single-pass removal efficiency as to aerosol particles with a diameter of 5 microns or greater with a liquid-to-gas ratio of about 15 gpm/1,000 cfm, or at least 99.9% single-pass removal efficiency as to aerosol particles with a diameter of 5 microns or greater with a liquid-to-gas ratio of about 20 gpm/1,000 cfm. The invention provides at least 99.9% double-pass removal efficiency as to aerosol particles with a diameter of 5 microns or greater.

The invention is also of a method of simultaneously purifying and conditioning air, comprising: receiving source air and an aqueous solution in a housing; receiving the source air via a drop charger and providing a spray of electrically charged drops of the aqueous solution to produce treated air; eliminating liquid in the treated air via a mist eliminator and producing conditioned air; receiving the conditioned air and producing supply air via a heat exchanger; and moving the supply air via a fan to a facility employing the supply air. The invention can additionally comprise providing the aqueous solution via a liquid purifier, preferably wherein the liquid purifier maintains a concentration of one or more disinfectants to destroy pathogens and other infectious agents and/or wherein the liquid purifier exposes the aqueous solution to ultraviolet light to destroy pathogens and other infectious agents. The invention provides at least 99.6% single-pass removal efficiency as to aerosol particles with a diameter of 5 microns or greater with a liquid-to-gas ratio of about 15 gpm/1,000 cfm, or at least 99.9% single-pass removal efficiency as to aerosol particles with a diameter of 5 microns or greater with a liquid-to-gas ratio of about 20 gpm/1,000 cfm. The invention provides at least 99.9% double-pass removal efficiency as to aerosol particles with a diameter of 5 microns or greater.

Further scope of applicability of the present invention, objects, and advantages will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 1-3 show expected removal efficiencies of the invention at three liquid-to-gas ratios;

FIG. 4 shows the expected toxic gas removal efficiency for the three different liquid-to-gas ratios;

FIG. 5 is a schematic diagram of the apparatus of the invention;

FIGS. 6-11 are psychometric charts of cases 1-6, respectively, discussed in the Experimental Results section, below.

DETAILED DESCRIPTION OF THE INVENTION

The present invention is of an apparatus and method for removing and destroying pathogens and toxic gases from air and simultaneously conditioning an air supply, especially for buildings. The invention is referred to by the acronym APC throughout this disclosure.

Figure 5:
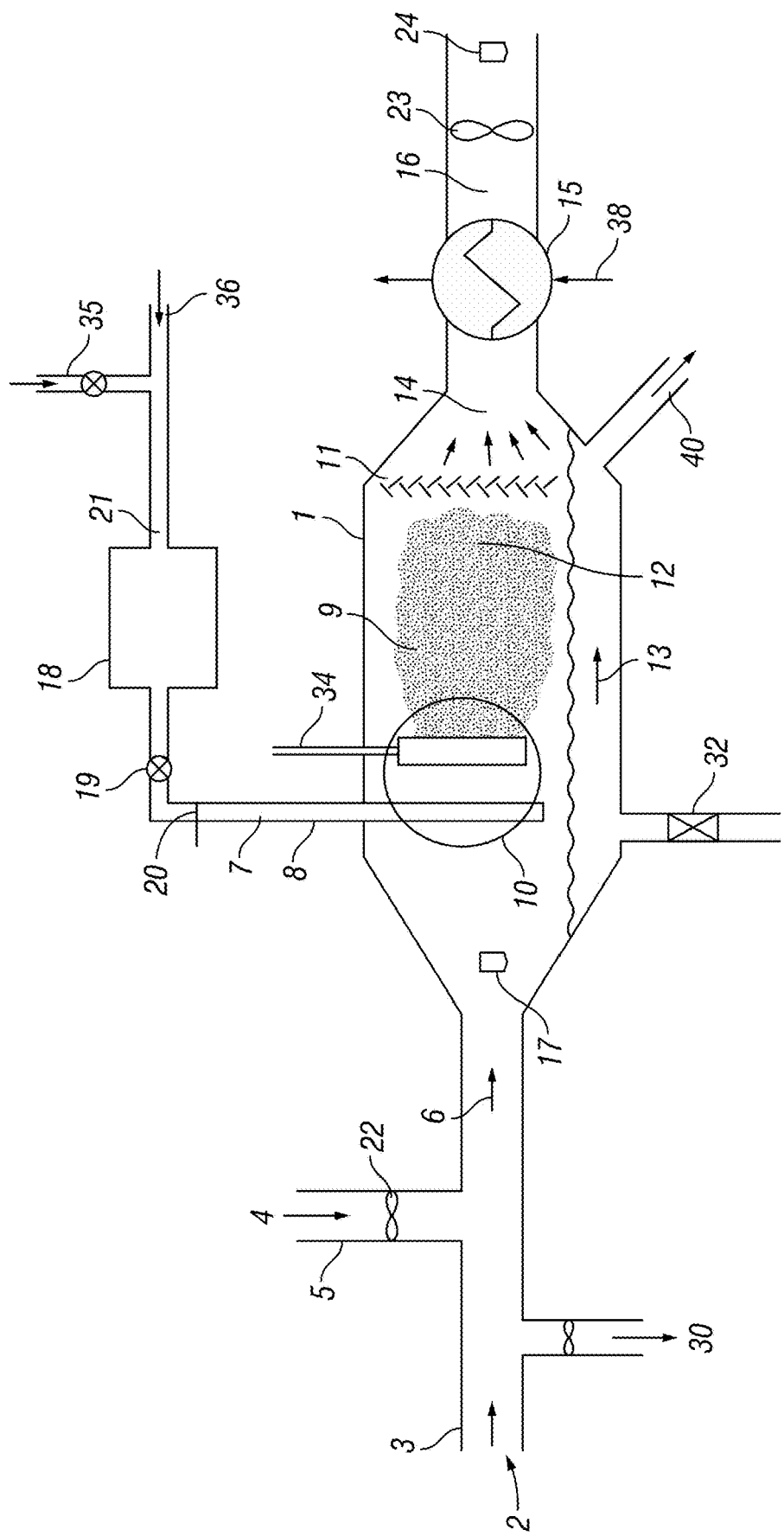
Figure 6:
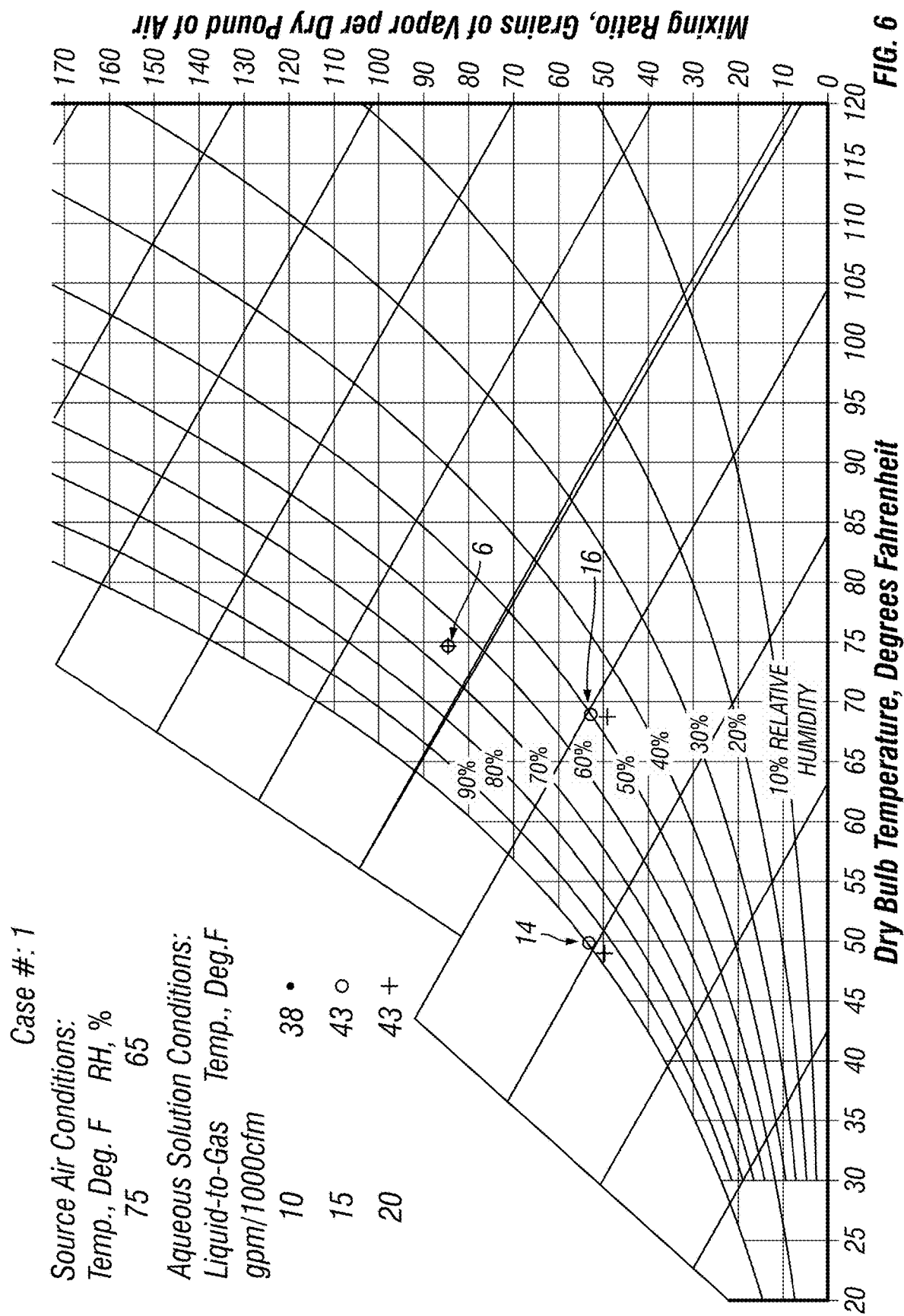
Figure 7:
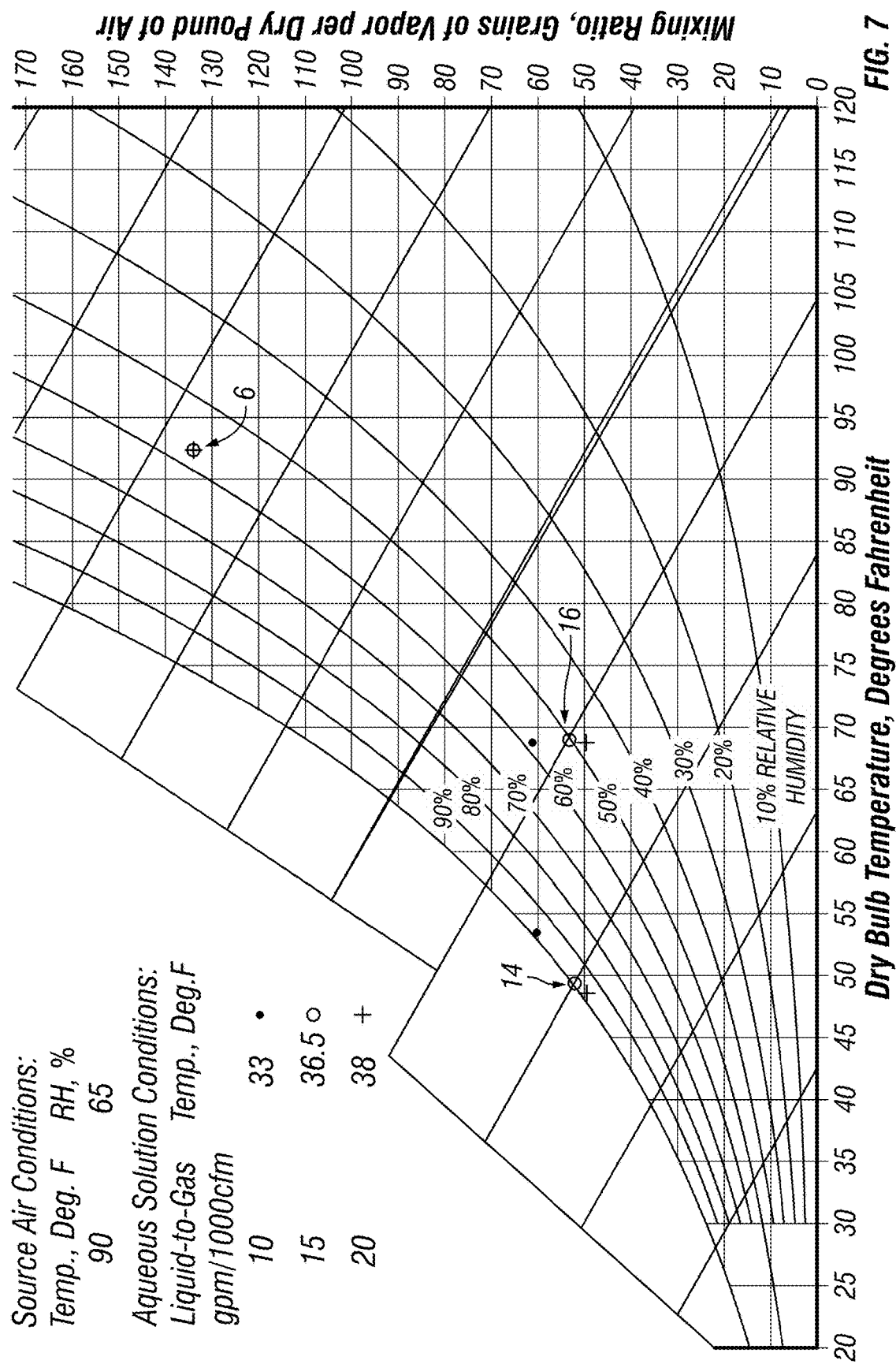
Figure 8:
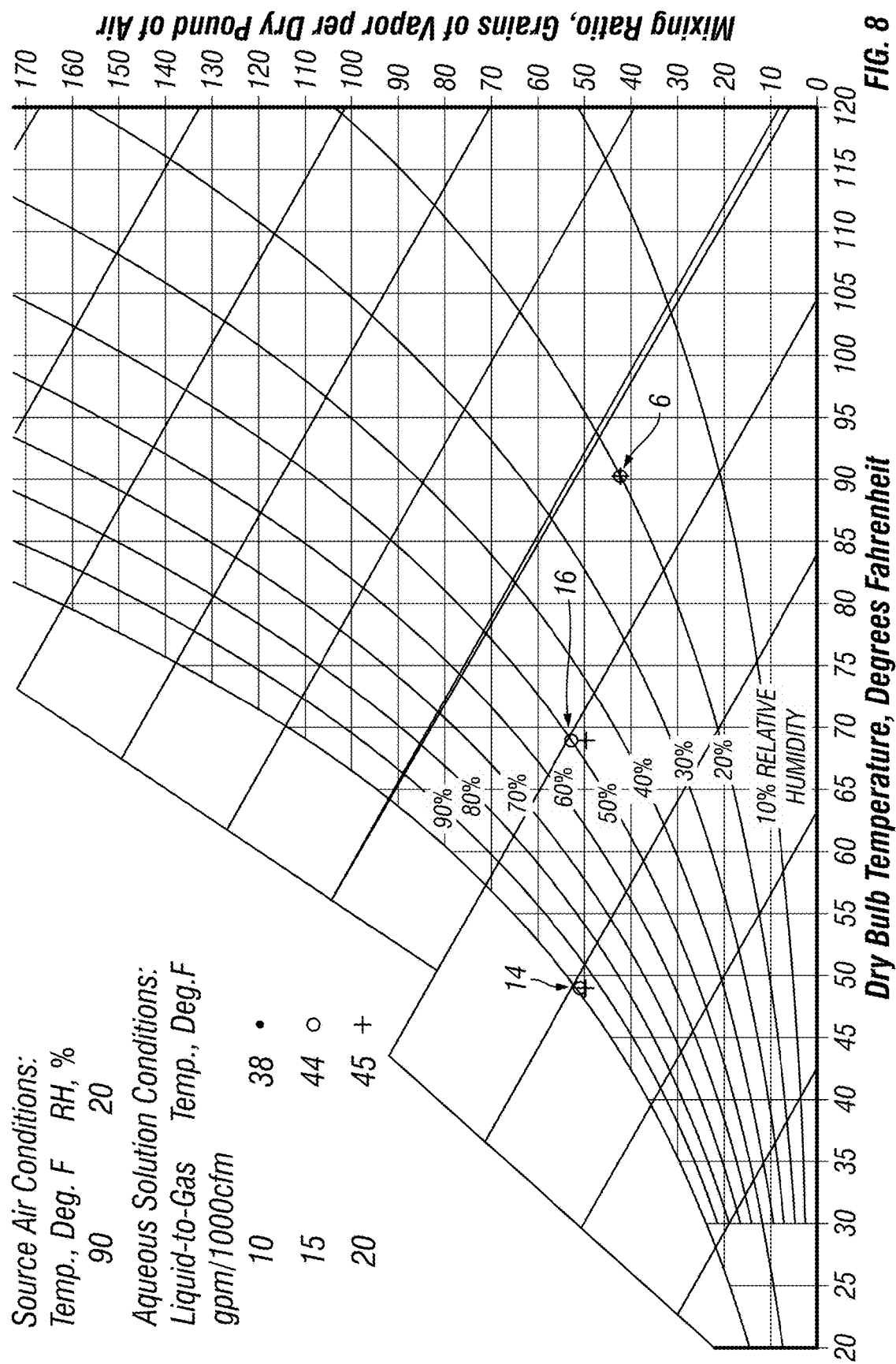
Figure 9:
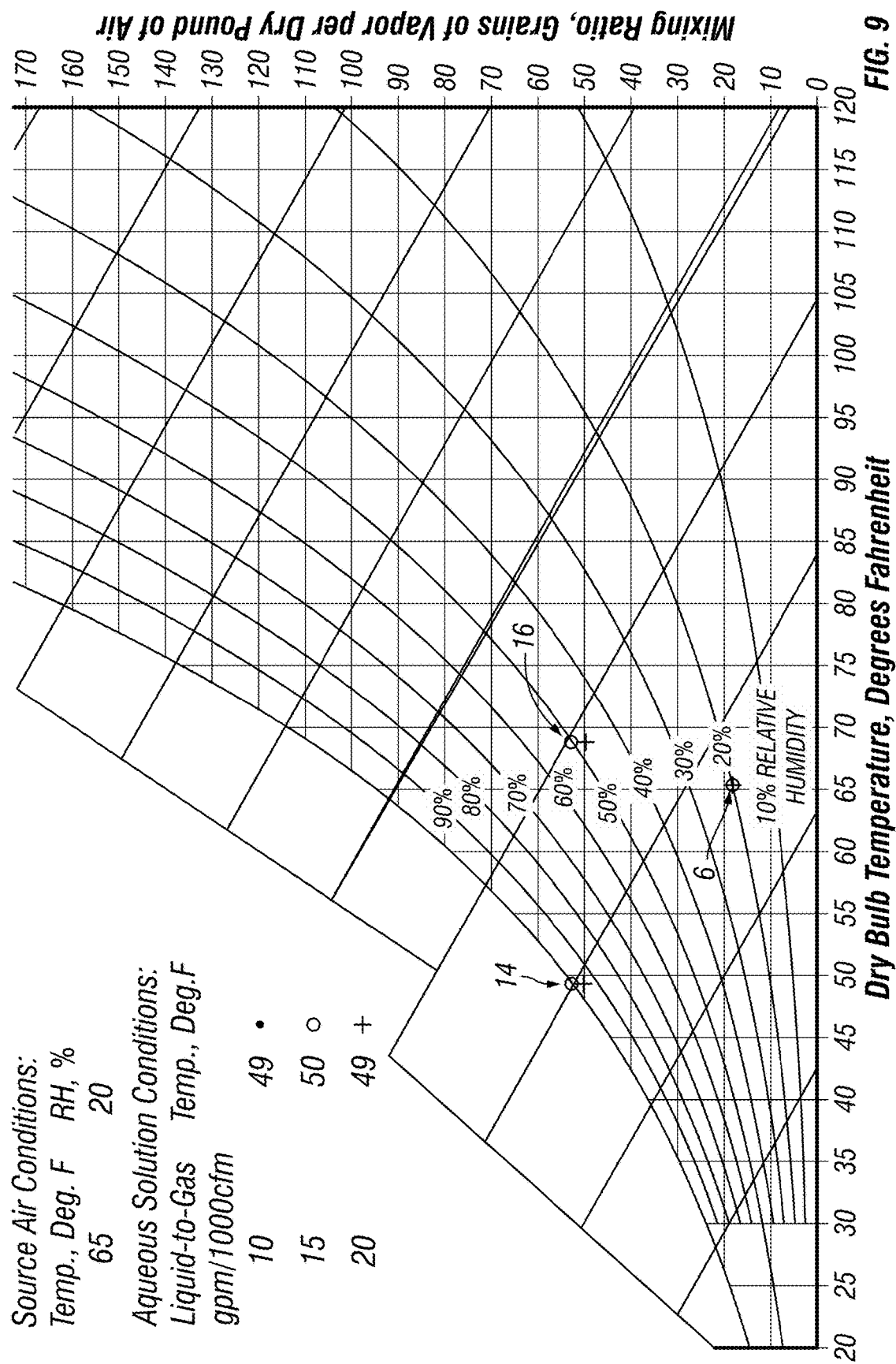
Figure 10:
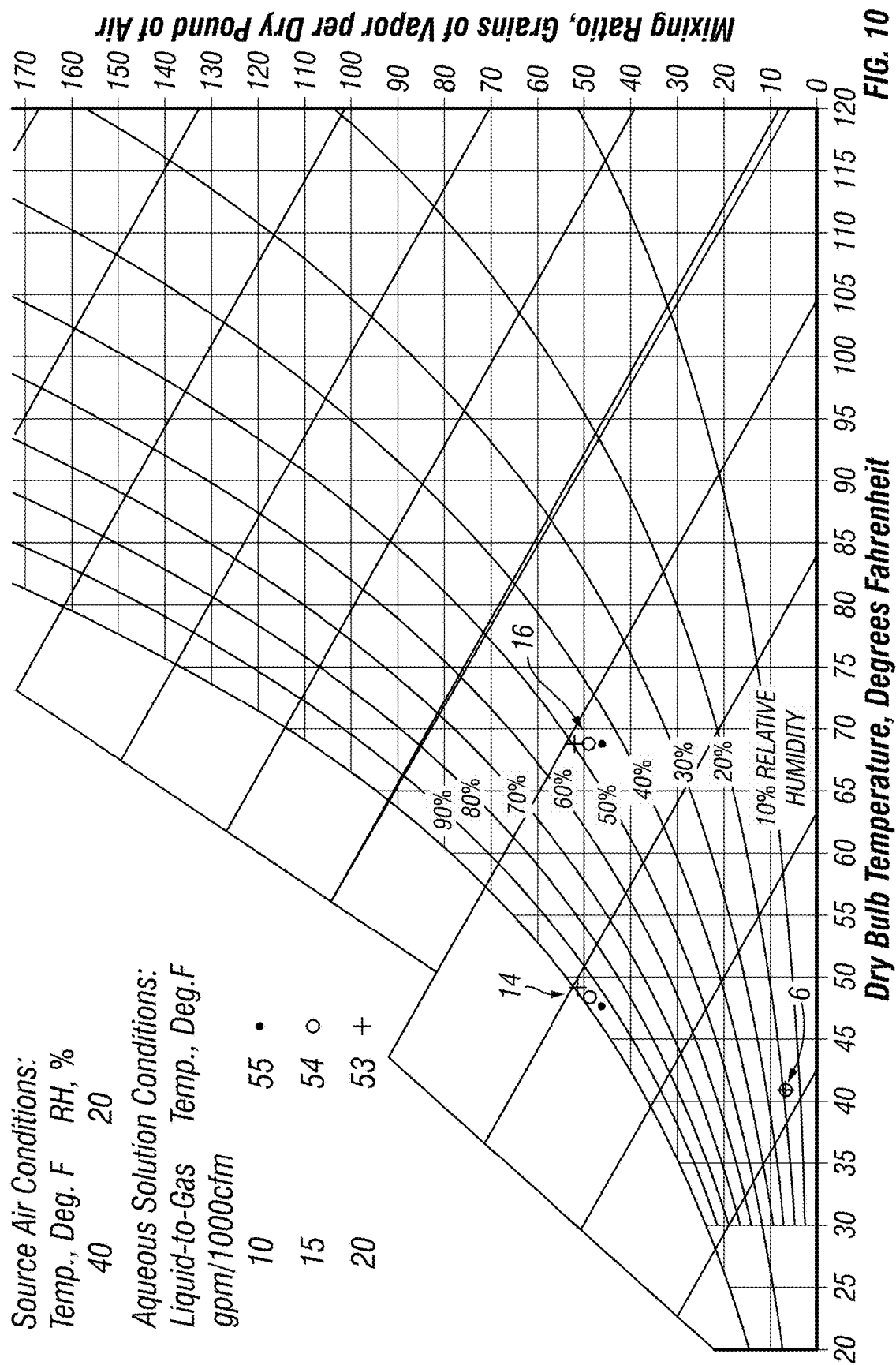
Figure 11:
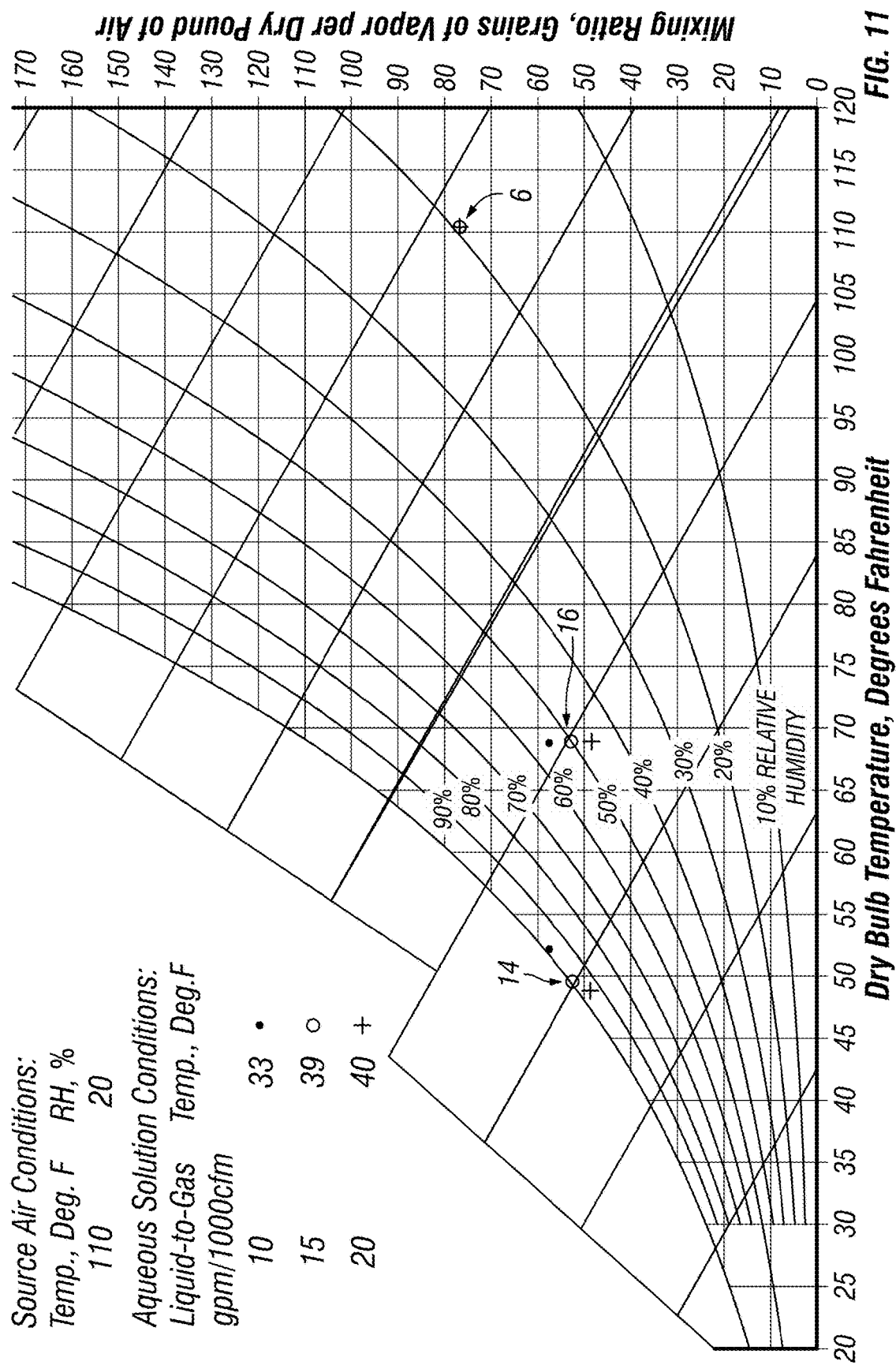

As shown in FIG. 5, the APC preferably comprises a housing 1 in which a combination of return air 2 from a building (or other facility) enters through duct 3 and is combined with fresh air 4 through fresh duct fan 5 by fresh air fan 22 to produce source air 6. An aqueous solution 7, chilled to a prescribed temperature, is introduced through pipe 8 and used to produce a spray of electrically charged drops 9 by drop charger 10. As the air/spray mixture travels through housing 1, the electrically charged drops 9 interact with source air 6, exchanging momentum, heat (enthalpy) and mass, while capturing aerosol particles which might contain pathogen particles and/or toxic gases contained in source air 6. By the time the air/spray mixture reaches mist eliminator 11, it has become treated source air 12. The mixture encounters mist eliminator 11 at the downstream end of housing 1 where mist eliminator 11 separates the liquid drops 9 from the treated source air 12. The captured liquid flows into sump 13 and the treated source air 12 exits housing 1 to produce liquid-free, cleaned and conditioned air 14. Conditioned air 14 then passes through heat exchanger 15 where the conditioned air 14 is heated to the temperature desired and returned to the building as supply air 16 by air supply fan 23. Additional components shown are sensor 17, liquid purifier 18, liquid flow rate meter 19, liquid temperature probe 20, concentration probe 21, sensor 24, exhaust air 30, blow down to sewer or water treatment 32, high voltage connection 34, water make-up 35, inlet from water cooler/heater 36, heat from water cooler/heater or furnace 38, and liquid return to water cooler/heater 40.

The APC preferably operates via the following steps:

Step 1. The operator must first choose the desired temperature and relative humidity for the supply air 16. This determines the desired mixing ratio of the supply air 16.

Step 2. The operator must choose the desired flow rate of the supply gas.

Step 3. The operator must choose the desired removal efficiency of pathogen particles and toxic gases. This determines the liquid-to-gas ratio to achieve that efficiency.

Step 4. Measure the relative humidity and temperature of the source air 6 using sensor 17.

Step 5. Calculate the aqueous solution temperature necessary to achieve the desired mixing ratio of supply air 16. This can be done with psychrometric charts or computer software.

Step 6. Adjust the liquid pumps (not shown) to supply the aqueous solution 7 flow rate as determined in Step 3.

Step: 7. Adjust the water chiller or water heater (not shown) that cools or heats the aqueous solution 7 to provide the temperature determined by Step 5.

Step 8. Maintain liquid purifier 18 such that all pathogens and toxic gases collected by the electrically charged drops 9 are deposited into sump 13. This can be done with one or a combination of methods:

a.) maintaining a concentration of disinfectants in the aqueous solution 7 that is necessary to destroy any pathogens or other infectious agents; and/or b.) expose the aqueous solution 7 to ultra violet light with an intensity sufficient to destroy the pathogens and infectious agents Step 9. Provide sufficient heat to the heat exchanger 15 to bring the conditioned air 14 to the desired temperature of the supply air 16. For example, this can be done by using exhaust heat from the water chiller's evaporator (not shown), a furnace (not shown), or a combination of the two or any other source of heat.

Step 10. It is important to note that all of the steps above can be automated by a controller by entering the parameters specified in Step 1 through Step 3, inputting the measurements made in Step 4, using software to perform Step 5, measuring the flow rate of aqueous solution 7 using liquid flow rate meter 19 to perform Step 6, using the liquid temperature probe 20 to perform Step 7, using concentration probe 21 to perform Step 8, and using temperature/relative humidity sensor 24 probe to perform Step 9.

The APC of the present invention has at least the following advantages over conventional HVAC systems:

a.) The APC removes and immediately destroys virtually all pathogens and toxic gases from the supply air to buildings. The use of electrically charged drops is a proven method to capture aerosol particulates from gas streams.

b.) The APC eliminates the need for humidifiers and de-humidifiers. The APC either evaporates water into the air or condenses water vapor from the air, depending upon the temperature and relative humidity of the source air.

c.) The APC incorporates of an inventive combination of proven technologies.

d.) The APC destroys pathogens and toxic gases immediately upon capture. HEPA filters trap aerosols, but the trapped aerosol matter resides on the filter fibers for days, until the filter is replaced. This allows the trapped aerosol matter to evaporate, if it is liquid. In which case, if there are virons or other pathogens with a diameter less than 0.3 microns in the aerosol matter, they will escape the filter and be re-entrained into the air flow.

e.) The APC eliminates the need for HEPA filters.

f.) The APC reduces the load on the supply fan 23 due to the added momentum acquired by the source air from the liquid drops while in the APC.

Experimental Results

Three computer programs, HUMMOM, COLLEFF, and COALEFF, were written to simulate the conditions in the APC as the air/spray mixture travels through housing 1. The purpose of the simulations was to determine the range of liquid-to-gas ratios which would provide over 99.9% removal efficiencies of aerosol particles with a diameter of 5 microns and greater with only a single pass through the APC. The aerosols particles which are the vectors for the spread of the virus SARS-CoV-2, which causes the COVID 19 disease, appear to be about 5 to 10 microns in diameter.

Figure 1:
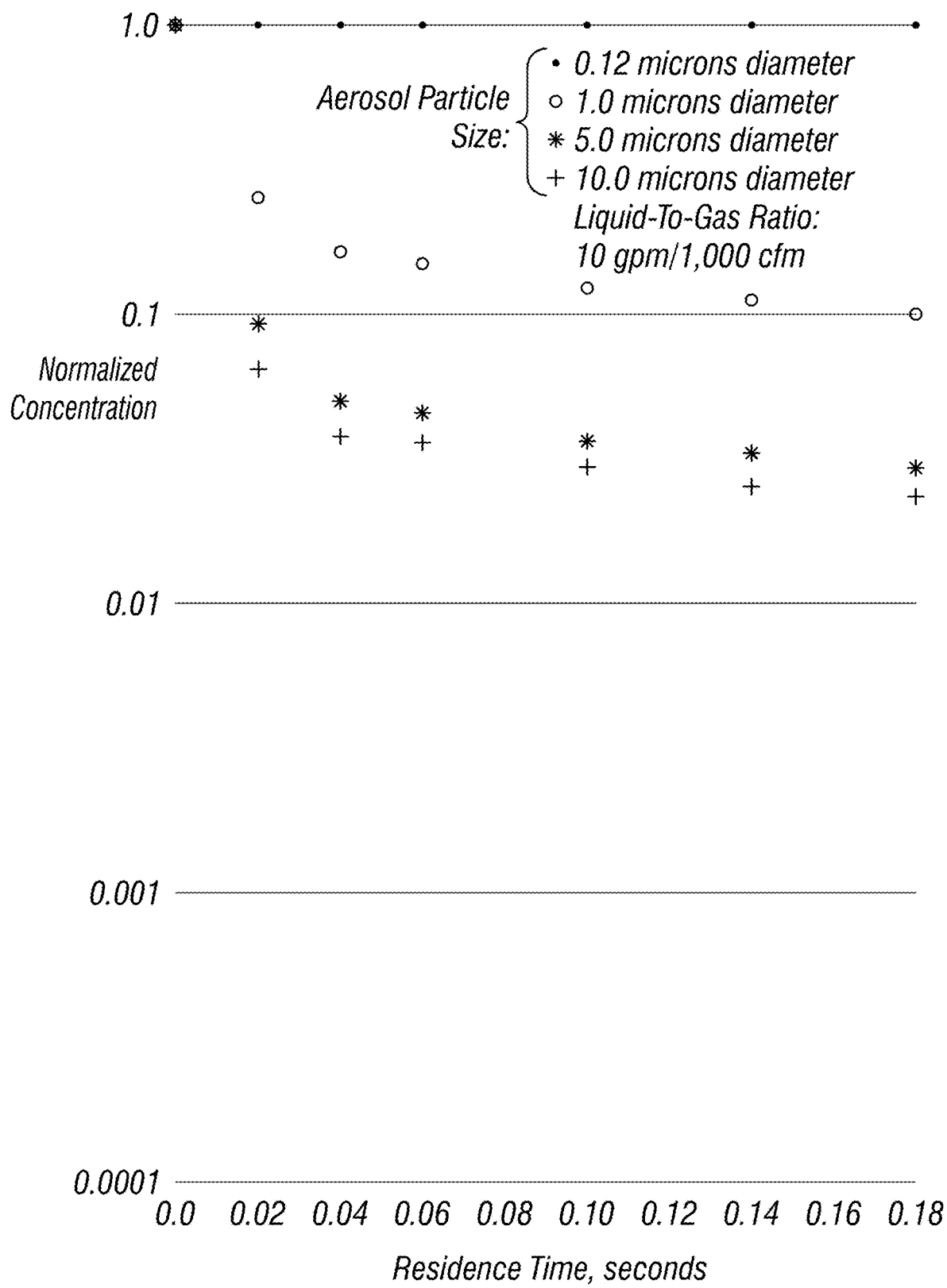
Figure 2:
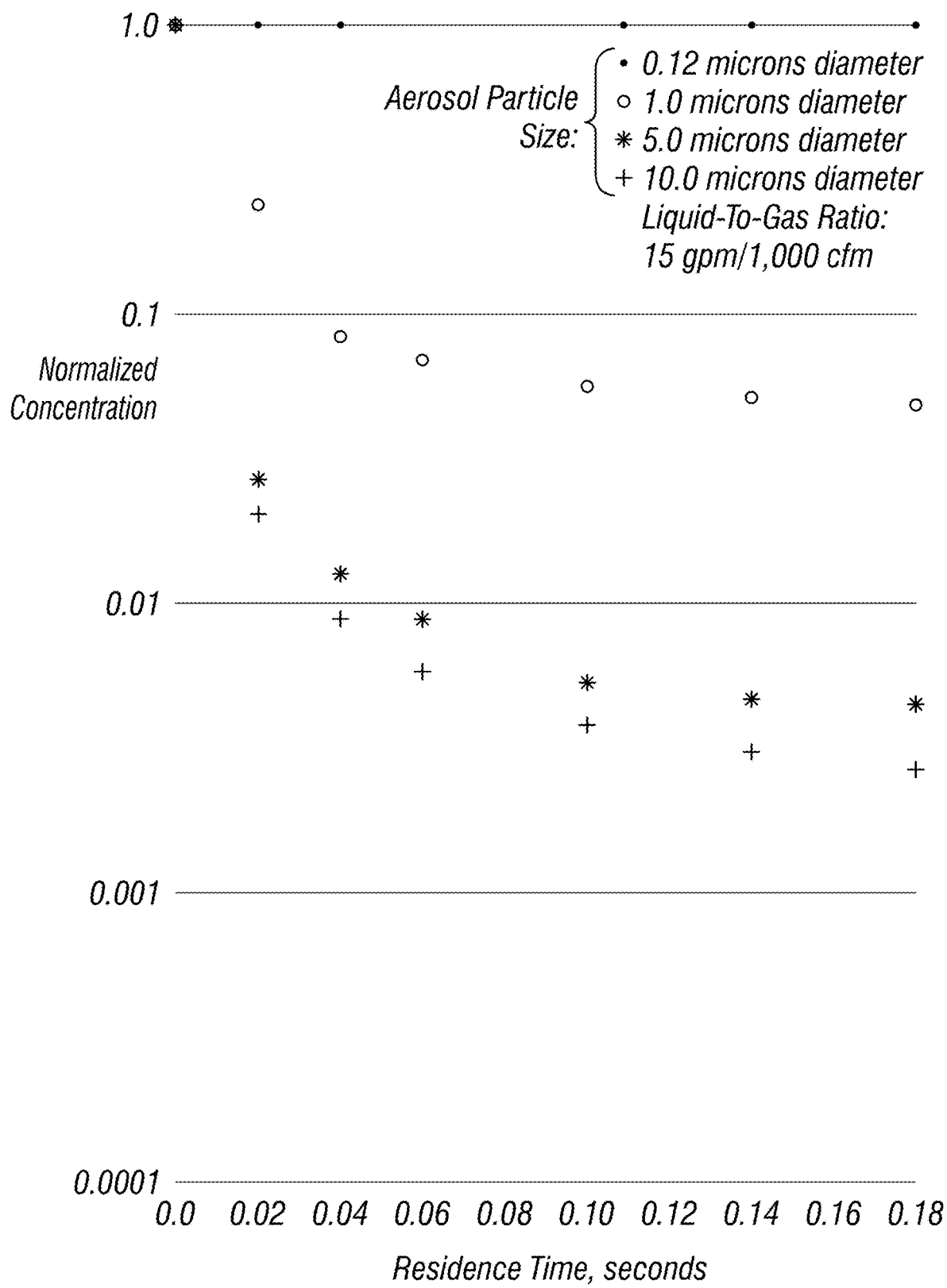

The removal efficiencies of three liquid-to-gas ratios are shown in FIGS. 1-3. The results shown in FIGS. 1-3 assume a charge on the drops of 10% of the Rayleigh limit and the aerosol particles are uncharged. The Sauter mean diameter of the drops is 122 microns.

Those results show that in order to achieve a 99.9% single pass removal efficiency of aerosol particles 5 microns and larger, a liquid-to-gas ratio must be 20 gpm/1,000 cfm (2.68 liters/m^3/sec). FIG. 2 shows that a 15 gpm/1,000 cfm (2.01 liters/m^3/sec) will provide a 99.6% removal efficiency in a single pass through.

These can be summarized as follows:

| Removal Efficiency for all Aerosol Particles 5 microns and larger: | Required Liquid-to-gas Ratio: |
|---|---|
| 98.8% | 10 gpm/1,000 cfm (1.34 liters/sec/m^3/sec) |
| 99.6% | 15 gpm/1,000 cfm (2.01 liters/sec/m^3/sec) |
| 99.9% | 20 gpm/1,000 cfm (2.68 liters/sec/m^3/sec) |

Figure 4:
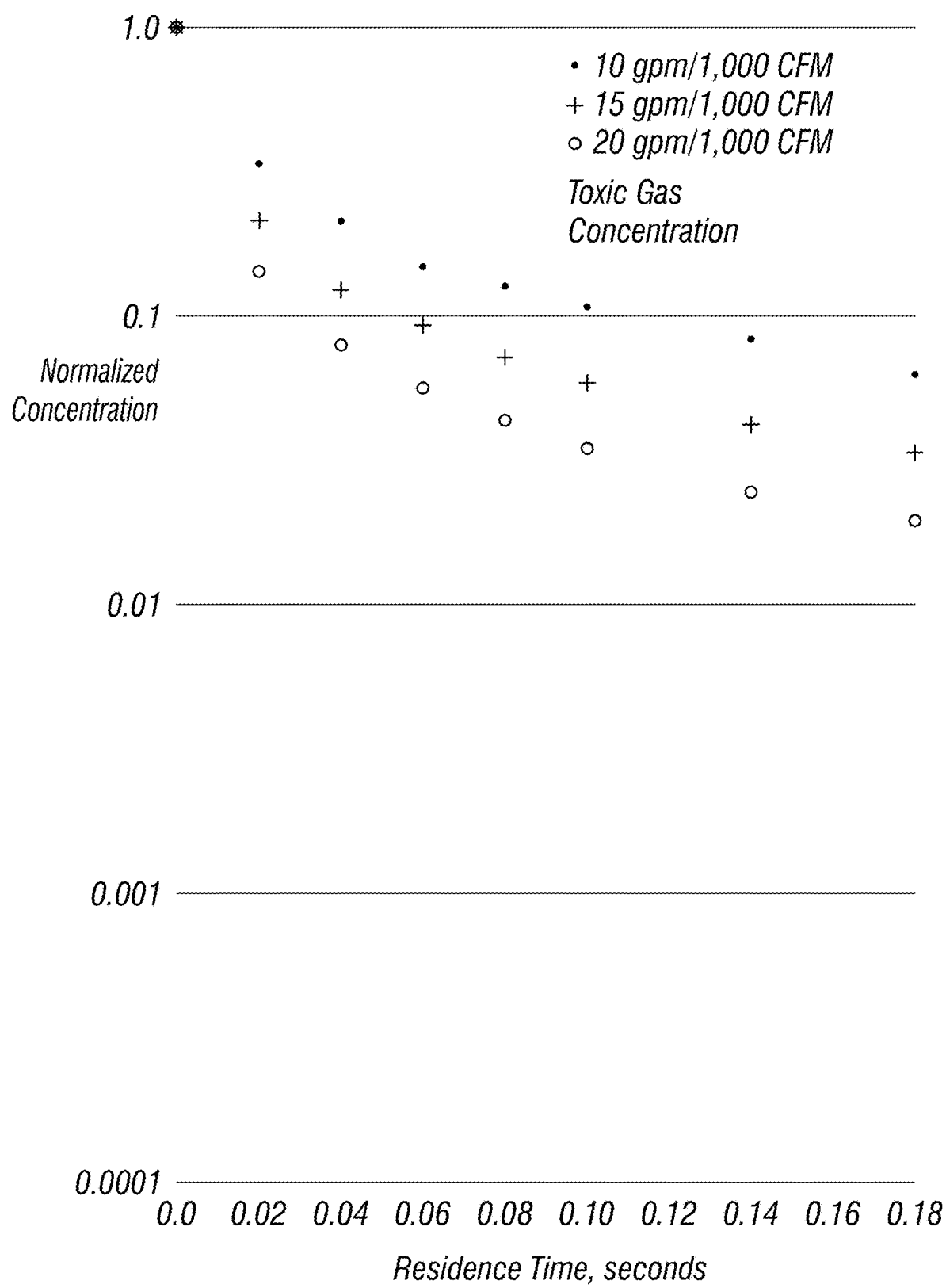

FIG. 4 shows the toxic gas removal efficiency for the three different liquid-to-gas ratios. It can be summarized as follows:

| Removal Efficiency of Toxic Gases: | Liquid-to-gas Ratio: |
|---|---|
| 93.5% | 10 gpm/1,000 cfm (1.34 liters/sec/m^3/sec) |
| 96.5% | 15 gpm/1,000 cfm (2.01 liters/sec/m^3/sec) |
| 98.1% | 20 gpm/1,000 cfm (2.68 liters/sec/m^3/sec) |

In each case, the aqueous solution 7 was assumed to have a vapor pressure of that of pure water. In practice, the agents added to aqueous solution 7 (as described in the Glossary), will lower the water vapor pressure of aqueous solution 7. That effect will result in a higher temperature of the conditioned air 14 than those shown in FIGS. 6-11, thus decreasing the temperature difference between the cleaned, conditioned air 14 and the supply air 16.

Six case studies, chosen to represent both typical and extreme return air conditions are plotted on psychrometric charts Case 1 through Case 6, in FIGS. 6-11.

Case 1 is taken to be a typical return air condition; it has been warmed slightly and the humidity has risen above the target conditions of 68 degrees F. and 45-50% relative humidity.

Cases 2-6 are situations seldom encountered by HVAC systems, but are included to demonstrate the ability of the APC to clean and condition air over a large range of temperatures and relative humidities.

| Source gas conditions: | | |
|---|---|---|
| | Air Temperature, F. | Relative Humidity,% |
| Case 1 | 75 | 65 |
| Case 2 | 90 | 60 |
| Case 3 | 90 | 20 |
| Case 4 | 65 | 20 |
| Case 5 | 40 | 20 |
| Case 6 | 110 | 20 |

These cases were simulated for three different liquid-to-gas ratios, 10 gpm/1,000 cfm (0.134 liters/sec/m^3/sec), 15 gpm/1,000 cfm (0.201 liters/sec/m^3/sec) and 20 gpm/1,000 cfm (0.268 liters/sec/m^3/sec).

For each liquid-to-gas ratio, the simulation program HUMMOM calculated the temperature of aqueous solution 7 which will best condition the treated source air 12 to a desired mixing ratio.

The desired mixing ratio will typically range from 47-53 grains of water vapor per pound of dry air (0.0070 to 0.00714 kg/kg). That mixing ratio range produces a relative humidity range of 45% to 50% when the conditioned air 14 is heated to 68 degrees Fahrenheit (20 degrees Centigrade) by heat exchanger 15.

The size distribution of the spray drops used in the simulations came from measurements made by the manufacturer of the nozzles. They have a Sauter mean diameter of 122 microns at a liquid pressure of 60 psig (414 KPa). (The same nozzles are in use in several installations using the methods taught by Richards (U.S. Pat. No. 6,156,098).)

The conclusion to be drawn from all of these results is that with a liquid-to-gas ratio in the range of 15-20 gpm/1,000 cfm (0.20 to 0.268 liters/sec/m^3/sec) will provide, in a single pass, proper conditioning, high pathogen particle removal and high toxic gas removal. Those liquid-to-gas ratios translate into dimensions of the housing 1 of about 10 feet wide by 10 feet tall by 15 feet in length for source air 6 flow rate of 50,000 cfm (23.6 m^3/sec).

ALTERNATIVE EMBODIMENTS

Alternate forms of the APC can use lower liquid-to-gas ratios and a shorter residence times. In fact, these forms will be preferred in most applications. They will provide the necessary conditioning and pathogen/toxic gas removal, but will require two or more passes through the APC. The time to meet those conditions depend on the ACH (air changes per hour), and the liquid-to-gas ratio. A case study of a typical application for a restaurant is shown in Case 7 (FIG. 11). The restaurant is assumed to be 4,000 square feet in area with a 10 foot ceiling and requires an ACH of 20 per hour, requiring an APC capable of handling 13,300 cfm. A liquid-to-gas ratio of only 5 gpm/1,000 cfm and a residence time of 0.2 seconds (in the APC) were chosen for this case, requiring a flow rate of 66.6 gpm of aqueous solution 7. The decrease of the concentration of toxic gases and particulate matter with time in the restaurant air is shown in below:

| | Concentration | | | |
|---|---|---|---|---|
| Time, | Toxic | Particle Size, microns | | |
| minutes | Gases | 1.0 | 5.0 | 10.0 |
| 0 | 1 | 1 | 1 | 1 |
| 3 | 0.133 | 0.3652 | 0.1770 | 0.1513 |
| 6 | 0.0179 | 0.1333 | 0.0313 | 0.0228 |
| 9 | 0.0024 | 0.0487 | 0.0055 | 0.0035 |
| 12 | 0.00032 | 0.0178 | 0.0010 | 0.00052 |
| 15 | 0.00004 | 0.0065 | 0.00017 | 0.00008 |
| 18 | 0.000006 | 0.0023 | 0.00003 | 0.00001 |

Concentration of Toxic Gases and Aerosol Particulates in Restaurant Air as a Function of Time The above shows that the APC will remove 99.999% of any toxic gases present within 20 minutes and remove over 99.9% of 5 micron size aerosol particles.

Using the same initial air and relative humidity as Case 1, the restaurant air comes to the target conditions of 50% relative humidity and 68 F in about 25 minutes, using a aqueous solution 7 temperature of 41 degrees F. and a liquid-to-gas ratio of 5 gpm/1,000 cfm.

These alternate forms could be configured such that the distance between drop charger 10 and mist eliminator 11 is only about three or four feet.

These configurations are possible because, as seen in FIGS. 1-3, the highest particulate removal takes place near the drop charger 10. This is due to the fact that the rate of exchange of momentum between the liquid and the air is greatest in that region.

Another alternate form would remove the outside air duct 5 and fresh air fan 23 from their upstream location and place them between heat exchanger 15 and air supply fan 23. This form would be recommended for situations in which the fresh air can be trusted to be free of contamination.

Yet another alternate form would treat the fresh air 4 with an air purifier before being introduced into return air 2 or supply air 16.

Still another alternate form would use any and all combinations of disinfectant agents or sterilization methods in liquid purifier 18 to insure that any pathogens or toxic gases are rendered harmless in aqueous solution 7 and fluid in sump 13. This could be intense UV irradiation, ozonation, use of chlorine, hypochlorites, quaternary ammonium compounds, etc.

In order to remove sub-micron sized pathogen particles, another alternate form would use the Particle Charger 20 of U.S. Pat. No. 6,986,803 to charge the particles with a polarity opposite the polarity of the electrically charged drops 9. This Particle Charger is preferably installed in the source air 6 about three feet upstream of drop charger 10.

Glossary

The following terms have the following meanings for this disclosure and the following claims:

ACH: Air changes per hour. This is the number of times the air in a building is changed. It varies from 1 per hour to 30 per hour; depending upon the type of building; office building, hospital, restaurant, etc. The typical value is 4 per hour.

Aqueous Solution: Water containing any combination of disinfectants, oxidizing agent, chemicals, or surfactants. The disinfectants and/or oxidizing agents are maintained at a concentration sufficient to kill living microorganisms and render harmless all other infectious agents. The chemicals are maintained at concentration sufficient to neutralize toxic gases and maintain a balance of pH between reasonable limits. Surfactant concentrations are maintained at a level sufficient to aid in attaching aerosol particulates with lipid surfaces to the surface of the electrically aqueous spray drops, as well as aid in the destruction of pathogens. The aqueous solution may also contain anti-foaming agents. The thermodynamic efficiency of the conditioning process is improved if an agent with a low vapor pressure (e.g., propylene glycol) is added to the to the solution.

Blowdown: The waste liquid bled off the system in order to maintain the concentration of solid particulate matter and chemical concentrations below certain limits and to maintain the sump liquid level between certain limits.

COALEFF: A computer simulation subprogram that calculates the coalescence efficiency between two liquid spray drops as they move with respect to each other. It uses the relative speed of the drops, along with the electrical charges (assumed to be of the same polarity) and the fluid flow forces to determine whether two drops will coalesce into a single drop as they approach each other.

COLLEFF: A computer simulation subprogram which calculates the removal efficiency of a single, electrically charged drop to collect aerosol particles in its path. It performs the calculation for any combination of drop size, particle size, electrical charge on either and any relative velocity.

Conditioned Air: Air that has a mixing ratio in a range of such that, when heated (or cooled) to 68 degrees Fahrenheit, will have a relative humidity in the range of 45%-50%.

Disinfectants: Chemical agents which kill living microorganisms and render harmless all other infectious agents.

Makeup Water: The fresh water injected into the system. It replaces the water in the system if the sump level goes below the low limit.

Drop Charger: Any method to produce copious quantities of liquid drops, each with a high electrical charge. As an example, the method taught by Richards (U.S. Pat. No. 6,156,098).

Dry gas: The fraction of gas that is non-condensable during the purifying/conditioning process.

Fresh Air: Outside air which is mixed with the return air from buildings in order to maintain desired levels of oxygen and carbon dioxide in the supply air.

HUMMOM: A computer simulation program which calculates the interchange of heat, momentum, mass and electrical charge between a spray of liquid drops and a gas containing aerosol particles and toxic gas. The input variables are: (1) Temperature and Relative Humidity of the source gas 6; (2) Temperature and Liquid-to-Gas Ratio of the aqueous solution 7; (3) Size distribution, velocity and charge of electrically charged drops 9; (4) Sizes and concentration of aerosol particles in the source gas 6; and (5) Concentration of toxic gases that are soluble in aqueous solution 7. The program uses these initial conditions to calculate the initial gas velocity and mixing ratio. All of these variables are then used to calculate the initial values for: (a) Total enthalpy of the source gas 6 and the aqueous solution 7; (b) Total momentum of the source gas 6 and the aqueous solution 7; (c) Total mass of water substance (water vapor in source gas 6 plus liquid water in aqueous solution 7); and (d) Total electrical charge on the aqueous solution 7 drops 9. Each of these totals are totals per mass of dry air. It then calculates the changes in all of these variables as it steps through small time intervals, checking the conservation of each of the totals. At each step, it calculates the change in the concentration of aerosol particulates and toxic gas.

HVAC Systems: Heating, Ventilation, and Air Conditioning Systems which provide cooling or heating of air for use as supply air to buildings. In some cases, the system also provides humidification or de-humidification of the air.

Liquid-to-Gas Ratio: The volume flow rate of liquid per volume flow rate of the source gas. Its units are Gallons per minute per 1,000 cubic feet per minute (gpm/1,000 cfm) (English) or Liters per second per cubic meter per second (liters/m^3/sec) (Metric). 1 gpm/1,000 cfm=0.134 liters/sec/m^3/sec.

Mixing Ratio: The mass of water vapor contained in a gas per unit mass of dry gas. It is unitless, but is usually given as Grains per pound (English) or Kilogram per kilogram (Metric).

Pathogen Particles: Aerosol particles containing any infectious agent such as a viron, prion, bacterium, protozoan, or fungus, as well as any aerosol particles containing algae or spores.

HEPA Filters: High-Efficiency Particulate Air filters, specified to be able to remove 99.97% of all particulates whose diameter is equal to 0.3 micrometer or larger.

Rayleigh Limit: The maximum amount of electric charge on a liquid drop, beyond which the electrical stresses on the drop overcome the surface tension stresses, causing it to break up into smaller drops.

Sauter Mean Diameter: The Sauter mean of a spray of drops is a measure of the total volume of all the drops to the total area of all the drops, equal to six times the ratio of those totals: D32=6*(Sum(Volumes)/Sum(Areas)).

Single Pass: One treatment of the source air 6 by the APC. This is the change which would occur to the return air 2 during a single air turnover of the building.

Supply Air: Air that is carried via ducts to a building or any facility requiring clean air at a specified humidity and temperature.

Surfactants: Surface active agents, made up of molecules that attach to both hydrophobic and hydrophilic particles or molecules.

Source Air: The air that is introduced into the air purifier/conditioner.

Viron: An individual virus particle, usually of size less than 1 micron, about 0.12 micron for SARS-CoV-2.

Note that in the specification and claims, "about" or "approximately" means within ten percent (10%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. An air purifier and conditioner comprising:
   a housing receiving source air and an aqueous solution;
   a drop charger receiving the source air and providing a spray of electrically charged drops of the aqueous solution to produce treated air;
   a mist eliminator eliminating liquid in the treated air and producing conditioned air;
   a liquid purifier providing the aqueous solution;
   a heat exchanger receiving the conditioned air and producing supply air; and
   a fan moving the supply air to a facility employing the supply air.

2. The air purifier and conditioner of claim 1 wherein said liquid purifier maintains a concentration of one or more disinfectants to destroy pathogens and other infectious agents.

3. The air purifier and conditioner of claim 2 wherein said liquid purifier additionally exposes the aqueous solution to ultraviolet light to destroy pathogens and other infectious agents.

4. The air purifier and conditioner of claim 1 wherein said liquid purifier exposes the aqueous solution to ultraviolet light to destroy pathogens and other infectious agents.

5. The air purifier and conditioner of claim 1 providing at least 99.6% single-pass removal efficiency as to aerosol particles with a diameter of 5 microns or greater.

6. The air purifier and conditioner of claim 5 wherein a liquid-to-gas ratio is about 15 gpm/1,000 cfm.

7. The air purifier and conditioner of claim 5 providing at least 99.9% single-pass removal efficiency as to aerosol particles with a diameter of 5 microns or greater.

8. The air purifier and conditioner of claim 7 wherein a liquid-to-gas ratio is about 20 gpm/1,000 cfm.

9. The air purifier and conditioner of claim 1 providing at least 99.9% double-pass removal efficiency as to aerosol particles with a diameter of 5 microns or greater.

10. A method of simultaneously purifying and conditioning air, the method comprising the steps of:
    receiving source air and an aqueous solution in a housing;
    receiving the source air via a drop charger and providing a spray of electrically charged drops of the aqueous solution to produce treated air;
    eliminating liquid in the treated air via a mist eliminator and producing conditioned air;
    providing the aqueous solution via a liquid purifier;
    receiving the conditioned air and producing supply air via a heat exchanger; and
    moving the supply air via a fan to a facility employing the supply air.

11. The method of claim 10 wherein the liquid purifier maintains a concentration of one or more disinfectants to destroy pathogens and other infectious agents.

12. The method of claim 11 wherein the liquid purifier additionally exposes the aqueous solution to ultraviolet light to destroy pathogens and other infectious agents.

13. The method of claim 10 wherein the liquid purifier exposes the aqueous solution to ultraviolet light to destroy pathogens and other infectious agents.

14. The method of claim 10 providing at least 99.6% single-pass removal efficiency as to aerosol particles with a diameter of 5 microns or greater.

15. The method of claim 14 wherein a liquid-to-gas ratio is about 15 gpm/1,000 cfm.

16. The method of claim 14 providing at least 99.9% single-pass removal efficiency as to aerosol particles with a diameter of 5 microns or greater.

17. The method of claim 16 wherein a liquid-to-gas ratio is about 20 gpm/1,000 cfm.

18. The method of claim 10 providing at least 99.9% double-pass removal efficiency as to aerosol particles with a diameter of 5 microns or greater.

* * * * *